US008561475B2

(12) United States Patent
Johnson et al.

(10) Patent No.: US 8,561,475 B2
(45) Date of Patent: Oct. 22, 2013

(54) METHOD AND APPARATUS FOR INVESTIGATING MECHANICAL PROPERTIES OF SOFT MATERIALS

(76) Inventors: Bruce David Johnson, Brookside (CA); Bernard Paul Boudreau, Halifax (CA); Mark Andrew Barry, Stillwater Lake (CA); Kelly Maureen Dorgan, La Jolla, CA (US); Peter Alfred Jumars, Whitefield, ME (US)

( * ) Notice: Subject to any disclaimer, the term of this patent is extended or adjusted under 35 U.S.C. 154(b) by 229 days.

(21) Appl. No.: 13/051,830

(22) Filed: Mar. 18, 2011

(65) Prior Publication Data
US 2012/0234102 A1    Sep. 20, 2012

(51) Int. Cl.
*G01N 3/08* (2006.01)
*G01B 5/30* (2006.01)

(52) U.S. Cl.
USPC .......................................................... 73/826

(58) Field of Classification Search
USPC .................. 733/760; 73/826, 830, 760
See application file for complete search history.

(56) References Cited

U.S. PATENT DOCUMENTS

| | | | |
|---|---|---|---|
| 3,707,119 A * | 12/1972 | Cowan .......................... 73/833 |
| 4,061,021 A | 12/1977 | Baldwin et al. |
| 4,594,899 A | 6/1986 | Henke et al. |
| 4,691,559 A * | 9/1987 | Fischer .......................... 73/81 |
| 4,806,153 A | 2/1989 | Sakai et al. |
| 5,515,294 A * | 5/1996 | Mohr et al. .................. 702/113 |
| 5,663,649 A | 9/1997 | Topp et al. |
| 5,726,349 A | 3/1998 | Palmertree et al. |
| 5,831,161 A | 11/1998 | Johnson et al. |
| 6,267,737 B1 * | 7/2001 | Meilus ......................... 601/108 |
| 6,289,734 B1 * | 9/2001 | Daugela ........................ 73/573 |
| 6,487,902 B1 * | 12/2002 | Ghosh ........................... 73/159 |
| 6,939,313 B2 * | 9/2005 | Saadat et al. ................. 600/587 |
| 7,040,146 B2 | 5/2006 | Mackenzie et al. |

OTHER PUBLICATIONS

Birkeland et al., "The Stuffblock Snow Stability Test", U.S. Forest Service Missoula Technology and Development Center, Publication No. 9623-2836-MTDC, 1996, pp. 1-14, USA.
Hallett et al., "A Simple Fracture Mechanics Approach for Assessing Ductile Crack Growth in Soil", Soil Science Society of America Journal, Jul.-Aug. 2001, pp. 1083-1088, vol. 65, Soil Science Society of America, USA.
Johnson et al., "Mechanical response to sediments in bubble growth", International Journal of Marine Geology, Geochemistry and Geophysics, 2002, pp. 347-363, vol. 187, Elsevier Science B.V.
Dorgan et al., "Burrow extension by crack propagation", Nature, Feb. 3, 2005, pp. 475, vol. 433, Nature Publishing Group, USA.
Boudreau et al., "Bubble growth and rise in soft sediments", Jun. 2005, Geology, pp. 517-520, vol. 33, No. 6, Geological Society of America, USA.

(Continued)

*Primary Examiner* — Max Noori
(74) *Attorney, Agent, or Firm* — James Marc Leas

(57) ABSTRACT

A method and apparatus for investigating subsurface properties of sediment, soil, snow, food stuff and other soft materials incorporates a probe head, preferably in the form of a coil spring that functions as a screw thread, which moves into the soil, snow, sediment, food stuff or other soft material, isolates a column of the material and applies tension to that column while measuring the applied force with a force sensor.

20 Claims, 5 Drawing Sheets

(56) References Cited

OTHER PUBLICATIONS

Taniwaki et al., "Device for acoustic measurement of food texture using a piezoelectric sensor", Mar. 2006, Food Research International, pp. 1099-1105, vol. 39, Elsevier Ltd.

McClung, D.M., "Fracture energy applicable to dry snow slab avalanche release", Jan. 2007, Geophysical Research Letters, vol. 37, American Geophysical Union, USA.

Jumars et al., "Material constraints on infaunal lifestyles: May the persistent and strong forces be with you", Mar. 26, 2007, Trace Fossils: Concepts, Problems, Prospects, ISBN 9780444529497, Elsevier Science.

Wang et al., "Experimental study on fracture toughness and tensile strength of a clay", Jun. 28, 2007, Engineering Geology, pp. 65-75, vol. 94, Elsevier B.V.

\* cited by examiner

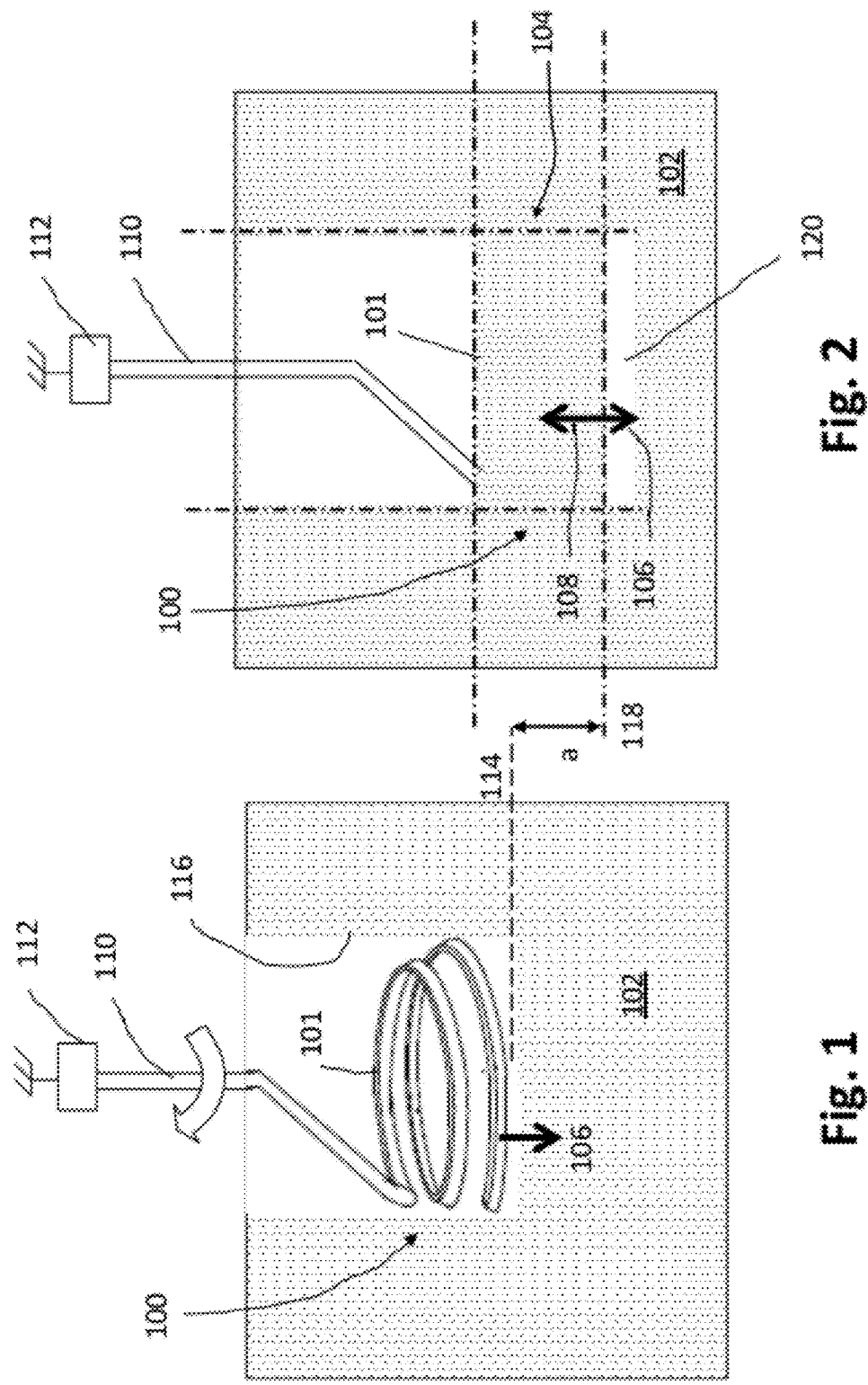

METHOD AND APPARATUS FOR INVESTIGATING MECHANICAL PROPERTIES OF SOFT MATERIALS

FIELD OF INVENTION

The invention relates to the field of probes for measuring the tensional strength or stress/strain character of materials that can be pierced such as sediment, soil, snow, food stuffs and/or other soft materials.

BACKGROUND OF INVENTION

It is often desired to measure the tensional strength or stress in a pierce-able material such as in sediment or soil. (Note that the term "tension" is utilized herein in the engineering sense of a stress that pulls on both ends of a member and not in the sense of the tenacity with which soil particles hold to water.)

The strength of soil, snow, sediment and other soft materials is a measure of the capacity of the material to resist deformation and can be understood in terms of the amount of energy required to break apart pieces of the material or move implements through the material or a measure of the amount of weight a given area of the material will support. Material failure may be in the form of permanent deformation through externally applied stress, e.g., sinking of a structure into the soil, breakup of the soil surface as in plowing; or alternatively failure may be from stresses affecting an unstable slope as in avalanches, mudslides, or erosion.

Soil strength tests are well established and described in multiple standard tests such as ASTM D1 194 (load plates), D1586 (standard penetration test), D3441 (cone penetration test), D4429 (bearing ratio in place) and ASAE S313.2 (soil cone penetrometer). All of these tests pertain to measurements made by compressing the test material. Similarly, testing of soils using a flat plate dilatometer for determining stress/strain characteristics (ASTM 6635-01) is also done using compression. A less common test for measuring the strength of soil determines shear strength as covered in ASTM D2573-08, Standard Test Method for Field Vane Shear Test in Cohesive Soil, or additionally ASTM STP 1014.

While measurements of compression and shear of soil, sediment, snow, food stuffs and other such pierce-able materials give important information about strength, there is additional information in measurements made with the sample in tension. In particular, the strength of materials in engineering studies is known to show differences depending on whether the test sample is subjected to compression or tension. For example, fibre reinforced materials typically show greater strengths in tension than in compression, and fibrous materials in soils and sediment are common. In addition, where a material contains defects, e.g., small cracks, tension can result in failure by fracture, whereas, compression may force small defects to close and not act as loci of failure.

Many studies of the strength of soil, snow, sediment, food stuffs and other such pierce-able materials have shown the importance of fracture as a mechanism of failure, e.g., failure of sediments during methane bubble growth and rise (see from reference list below Johnson et al., 2002; Boudreau et al., 2005); failure of sediments during animal locomotion (Dorgan, et al. (2005) and Jumars et al. (2007)); failure of soils (e.g., Wang, et al., 2007; Hallet and Newson, 2001); failure of snow (e.g., McClung, 2007); failure of foodstuff (e.g., Scanlon and Long, 1995). However, probes for measuring the strength of soil, snow, sediment, foodstuffs and other such pierce-able material have measured compression or shear strength, and laboratory measurements have typically relied on engineering type sample compression or tension loading or three point bending or cantilever tests. In our understanding, there are at present no in situ probes for measuring failure of soil, snow, sediment, foodstuff and other such pierce-able materials in tension.

In situ probe measurements can provide information on material strength at small intervals of distance, whereas typical engineering measurements on samples in tension or compression cause the sample to fail only at its weakest point which provides only a single datum for that sample. While in situ probes offer advantages in resolution of material strength over distance, current in situ probes typically measure compression or shear failure. This is a problem because the strength of sediment, soil, snow, foodstuff or other such pierce-able materials in tension is important for identifying discontinuities or other regions of weakness that may result in slumping or failure as in mud slides and avalanches or may indicate regions of weakness that may result in erosion or other modes of failure. Measurement of materials in tension is superior to measurement in compression for identifying dislocations, defects, and weak layers since compression presses surfaces together rather than pulling them apart.

Further, measurements of failure in tension provide different information than failure in shear because shear strength can be enhanced through interlocking of grains of sand or gravel, or granular snow or ice. Shear may actually close defects that tension will open and cause material failure. For example, measurements of compression and shear failure on clean sand show a much greater strength than measurements of tension on the same material. The difficulty of interpreting measurements from a compressive type probe are apparent in use of the cone penetrometer, a type of probe often used to determine strength of soil and sediments. This device uses a cone shaped probe head that is driven into the soil either at constant speed or with constant force and the resistance to penetration is measured with a force sensor. Considerable effort has gone into improving this method by adding sensors to measure friction force and pore water pressure. Still, difficulty in interpreting cone penetrometer measurements in terms of type of material, e.g., sand, silt, gravel, etc., requires typically that samples of the material be collected and assessed.

In determining the strength of snow to assess the risk of avalanches methods are often simple and effective, but do not provide information on material strength other than failure under the conditions of the test. This means that while a particular test may show the snow to be safe, there is not sufficient information to determine if small changes in conditions, e.g., moisture content, temperature, etc., might make the snow pack prone to failure. Commonly used methods for measuring stability of snow against avalanches typically involve digging snow pits and then determining the stability when applying stress at the surface. One example is the stuffblock test (Birkeland, K. W., R. F. Johnson and D. Herzberg. 1996). In this test a bag filled with 10 lbs of snow is dropped from various heights onto a column of snow at the edge of a snow pit. In application of this method the snow fails typically at a single point, whereas, measurements with an in situ probe that measures failure under tension could provide measurements of material strength over small depth intervals and thereby identify regions that may be near failure and that may fail if the conditions change.

Force measurements in food assessments typically involve: puncture, compression-extrusion, cutting-shear, compression, tension, torsion, bending and snapping and deformation. Tension measurements are typically done with samples of specific dimensions subjected to typical engineering testing to determine elongation and failure. Probes used for assessing foods are typically for measurement of puncture strength, moisture or thermal properties.

Mitsuru Taniwaki, et al., developed a method for assessing food texture in which a probe is inserted into a food sample and the vibration caused by the sample's fracture is detected using a piezoelectric sensor. The method follows previous work in which the sounds of food mastication were recorded. Results show promise for assessing food texture, but have not proven useful for quantifying fracture strength.

A variety of probes are disclosed in the patent literature. U.S. Pat. No. 4,806,153 discloses a penetrometer for soils that uses sensors to measure compressive resistance to penetration, friction from penetration and pore water pressure. U.S. Pat. No. 5,831,161 discloses a penetrometer for snow that measures compressive resistance to penetration using a force transducer. U.S. Pat. No. 7,040,146 discloses a soil and snow penetrometer that uses sensors to measure the compressive resistance to penetration of a probe head into soil and snow. It uses a load cell and accelerometer and a processor to interpret results in terms of the compressive vertical strength of soil or snow. U.S. Pat. Nos. 4,061,021, 5,726,349, 5,663,649 also describe probes that measure compressive strength of soils and other soft materials.

In addition, probes have been described for measuring shear strength and Young's modulus of soils, snow and sediments, including U.S. Pat. No. 4,594,899 which describes a probe for soil that is comprised of two concentric cylinders. When inserted into the soil, the rotary response of the inner cylinder is measured in response to a known rotary excitation and is interpreted in terms of the soil liquefaction resistance and soil degradation.

Despite the considerable art in the field, a need still exists for an in situ method and apparatus for measuring the tensional strength of soil, snow, sediment, foodstuff and other such pierce-able materials.

REFERENCES CITED

A. Birkeland, K. W., R. F. Johnson and D. Herzberg. (1996) The stuff block snow stability test. Technical Report 9623-2836-MTDC. U.S. Department of Agriculture Forest Service, Missoula Technology and Development Center, Missoula, Mont., 20 pp.
B. Boudreau, B. P., Algar, C., Johnson. B. D., Croudace, I., Reed, A., Furukawa, Y., Dorgan, K. M., Jumars, P. A., Grader, A. S. & Gardiner, B. S. (2005). Bubble growth and rise in sediments. Geology 33, 517-520.
C. Dorgan, K. M., Jumars, P. A., Johnson, B. D., Boudreau, B. P. & Landis, E. (2005). Burrow extension by crack propagation. Nature 433, 475.
D. Hallett, P. D. & Newson, T. A. (2001). A simple fracture mechanics approach for assessing ductile crack growth in soil. Soil Science Society America J. 65, 1083-1088.
E. Johnson, B. D., Boudreau, B. P., Gardiner, B. & Maass, R. (2002). Mechanical response of sediments to bubble growth. Mar. Geol. 187, 347-363.
F. Jumars, P. A., Dorgan, K. M., Mayer, L. M., Boudreau, B. P., & Johnson, B. D. (2007). Material constraints on infaunal lifestyles: may the persistent and strong forces be with you. Chapter 29. In Trace Fossils: Concepts, Problems, Prospects. Elsevier Press.
G. McClung, D. M. (2007). Fracture energy applicable to dry snow slab avalanche release. Geophys. Res. Let., 34, LO2503, 5 pages)
H. Taniwaki, M., T. Hanada and N. Sakurai (2006). Device for acoustic measurement of food texture using a piezoelectric sensor. Food Research International, Volume 39, Issue 10, December 2006, 1099-1105.
I. Wang, J.-J., Jhu, J.-G., Chiu, C. F. &. Jhang, H. (2007). Experimental study on fracture toughness and tensile strength of a clay. Engineering Geol. 94, 65-75.
J. U.S. Pat. No. 4,061,021 December 1977 Baldwin et al
K. U.S. Pat. No. 4,594,899 June 1986 Henkeetal.
L. U.S. Pat. No. 4,806,153 February 1989 Sakaietal.
M. U.S. Pat. No. 5,663,649 September 1997 Toppetal.
N. U.S. Pat. No. 5,726,349 March 1998 Palmertree et al.
O. U.S. Pat. No. 5,831,161 November 1998 Johnson et al.
P. U.S. Pat. No. 7,040,146 May 2006 Mackenzie et al.

SUMMARY OF INVENTION

One aspect of the invention provides a method for determining the tensile strength of a material. The method includes the steps of: (a) provisioning a probe comprising a housing and a longitudinal member rotatable in the housing, where the longitudinal member terminates in a coil spring thread that is situated external to the housing; (b) positioning the coil spring thread at a first depth in the material; (c) rotating the longitudinal member so as to pull the coil spring thread into the material and generate a reactionary pull substantially in a columnar portion of the material scored by the coil spring thread, following which the terminating end of the coil spring thread will be pulled to a second depth; (d) measuring a strain on the longitudinal member as the coils spring head moves to the second depth; and (e) determining the strength of the material based on the measured strain.

The columnar portion of the material may fracture at the second depth. In this case, the fracture strength of the material may be determined based on the measured strain at the second depth, a difference between the first and second depths, and a diameter of the coil spring thread.

The coil spring thread is preferably configured such that the reactionary force generated by it is directed inwardly towards the columnar portion of the material surrounded by the coil spring thread. To achieve this, coil spring thread preferably has a generally rectangular cross-sectional profile including a top corner proximate the longitudinal member and a diametrically opposed bottom corner distal the longitudinal member, the coil spring thread being canted so that the top corner is closer to a central axis of the coil spring thread than the bottom corner.

In an extension of the method, the probe may be moved to successively increase the first depth and steps (c) to (e) repeated. This enables a discrete plot of the tensile strength of the material relative to the depth of the material.

In an alternate extension of the method, the probe may be continuously moved deeper into the material at a predetermined rate that is less than a rate at which new material is drawn into the coil spring thread as a consequence of continuously rotating the longitudinal member. In this manner, stress can be built on successive columnar samples of the material as the probe is advanced into the material. Steps (d) and (e) are repeated to thereby continuously plot the tensile strength of the material relative to the depth of the material.

In any extension of the method, as the probe creates a bore in the material and the fracturing of columnar material samples yields loose materials that may affect the fracture signal, the method preferably includes clearing such loose material out of the bore.

Another aspect of the invention provides a probe apparatus for determining the tensile strength of a material. The apparatus includes a housing; a longitudinal member rotatably journaled in the housing, the longitudinal member defining a longitudinal axis; a coil spring thread, rigidly connected to the longitudinal member, and disposed external of the housing; a mechanism for rotating the longitudinal member and coil spring thread, wherein, upon rotation of the longitudinal member and coil spring thread, the coil spring thread is pulled into the material causing a stress on the longitudinal member and generating a reactionary pull in the material; a strain gauge for measuring the stress on the longitudinal member relative to the housing; and a controller connected to the strain gauge for determining the tensile strength of the material based on the stress experienced by the longitudinal member.

The controller preferably measures the stress experienced by the longitudinal member when the material fractures due to the reactionary pull.

As discussed above, the coil spring thread is preferably configured such that the reactionary force generated by it is directed inwardly towards the columnar portion of the material surrounded by the coil spring thread. To achieve this, coil spring thread preferably has a generally rectangular cross-sectional profile including a top corner proximate the longitudinal member and a diametrically opposed bottom corner distal the longitudinal member, the coil spring thread being canted so that the top corner is closer to a central axis of the coil spring thread than the bottom corner The coil spring thread may be helical and concentric with the longitudinal member. The helical coil spring thread may have at least two volutes, one volute being proximate to the longitudinal member and one volute being distal to the longitudinal member, the distal volute having a diameter larger than the proximate volute. A transition portion may continue the longitudinal member and connect it with the proximate volute of the coil spring thread.

The probe may also include a hollow shaft rotatably mounted to the housing. The longitudinal member is disposed within the hollow shaft and the coil spring thread is disposed external of the hollow shaft. The hollow shaft having an auger blade connected to the outer wall of the shaft, the hollow shaft being rotated by the motor or an another motor. The auger is preferably provided for clearing loose material out of the bore created by the probe.

To move the probe downwardly, a moving stage may be mounted to translate linearly within the housing and a motor provided for driving the moving stage. The hollow shaft and the longitudinal member depend from the moving stage, and the controller controls the rate of decent of the moving stage which, in turn will control the probe rate of decent. Preferably, the controller controls the linear translation rate of the moving stage and decent of the hollow shaft such that this rate is less than the rate at which new material is fed into the coil spring head, thereby enabling stress to build up in the column of material surrounded by the coil spring thread until the column fractures.

Another aspect of the invention provides a method for determining the tensile strength of a material. The method includes the steps of: (a) provisioning a probe comprising a housing having a longitudinal axis and a coil spring thread that is movably connected the housing rotationally and longitudinally; (b) rotating the coil spring thread such that said rotating drives the coil spring thread into the material to hold a volume of material therein, (c) generating a longitudinal force in the coil spring thread to urge the volume of material longitudinally away from remaining material, wherein the longitudinal force is resisted by adherence of the volume of material to the remaining material, (d) increasing the longitudinal force until the volume of material separates from the remaining material; and (e) determining the tensile strength of the material based on the longitudinal force applied in step (d) at the time the volume of material separated from the remaining material.

In one variant of this aspect of the invention, steps (b), (c) and (d) occur simultaneously. This may be accomplished, for instance, by rotating the longitudinal member in situ (where the vertical position of the longitudinal member is fixed relative to the housing), in which case, provided the coil spring thread has enough grip in the material, the rotation of the coil spring thread generates the longitudinal force in the coil spring and the reactionary force in the material, the longitudinal force increasing as the coil spring thread gets pulled deeper into the material until the volume of material separates from the remaining material. This may also be accomplished by continuously moving the longitudinal member and coil spring thread deeper into the material at a predetermined rate that is less than a rate at which new material is drawn into the coil spring thread as a consequence of it continuous rotation, in which case the longitudinal force increases as the coil spring thread gets moves deeper into the material at a faster rate than the rate of descent, until the volume of material separates from the remaining material.

In another variant of this aspect of the invention, step (b) may occur separately than steps (c) and/or (d). This may be accomplished by first rotating the longitudinal member and coil spring member whilst enabling these components to freely move longitudinally into the material. Then, a longitudinal force is applied to the longitudinal member and the coil spring thread to urge the volume of material longitudinally away from remaining material. The longitudinal force is then increased until the volume of material separates from the remaining material.

In another aspect, the invention is directed to a method for determining the tensile strength of a material, including:
(a) driving a material engagement head into the material to hold a volume of material therein, wherein the material engagement head has a longitudinal axis;
(b) generating a longitudinal force in the material engagement head to urge the volume of material longitudinally away from remaining material, wherein the longitudinal force is resisted by adherence of the volume of material to the remaining material;
(c) increasing the longitudinal force until the volume of material separates from the remaining material; and
(d) determining the tensile strength of the material based on the longitudinal force applied in step (c) at the time the volume of material separated from the remaining material.

In another aspect, the invention is directed to a probe for determining the tensile strength of a material, comprising a housing having a longitudinal axis, a material engagement head, disposed external of the housing and movable longitudinally relative to the housing, a motor system operatively connected to the material engagement head and operable to drive the material engagement head into the material, wherein the material engagement head is shaped to hold and engage a volume of material, wherein the motor system is further operable to exert a longitudinal force on the material engagement head, wherein the material engagement head is shaped to transmit the longitudinal force into the volume of material to urge the volume of material longitudinally away from remaining material, wherein the motor system is operable to progressively increase the longitudinal force, a sensor positioned to sense the longitudinal force applied by the motor system, and a controller for receiving signals from the sensor, wherein the controller is programmed to determine the longitudinal force applied at the time that the volume of material separated from the remaining material.

BRIEF DESCRIPTION OF THE DRAWINGS

The foregoing and other advantages of the invention will be better appreciated having regard to the following drawings, in which:

FIGS. 1 and 2 are schematic representations of the subsurface testing of the tensile strength of a test material using a probe tip according to a preferred embodiment of the invention.

DETAILED DESCRIPTION OF PREFERRED EMBODIMENTS

Figure 3:
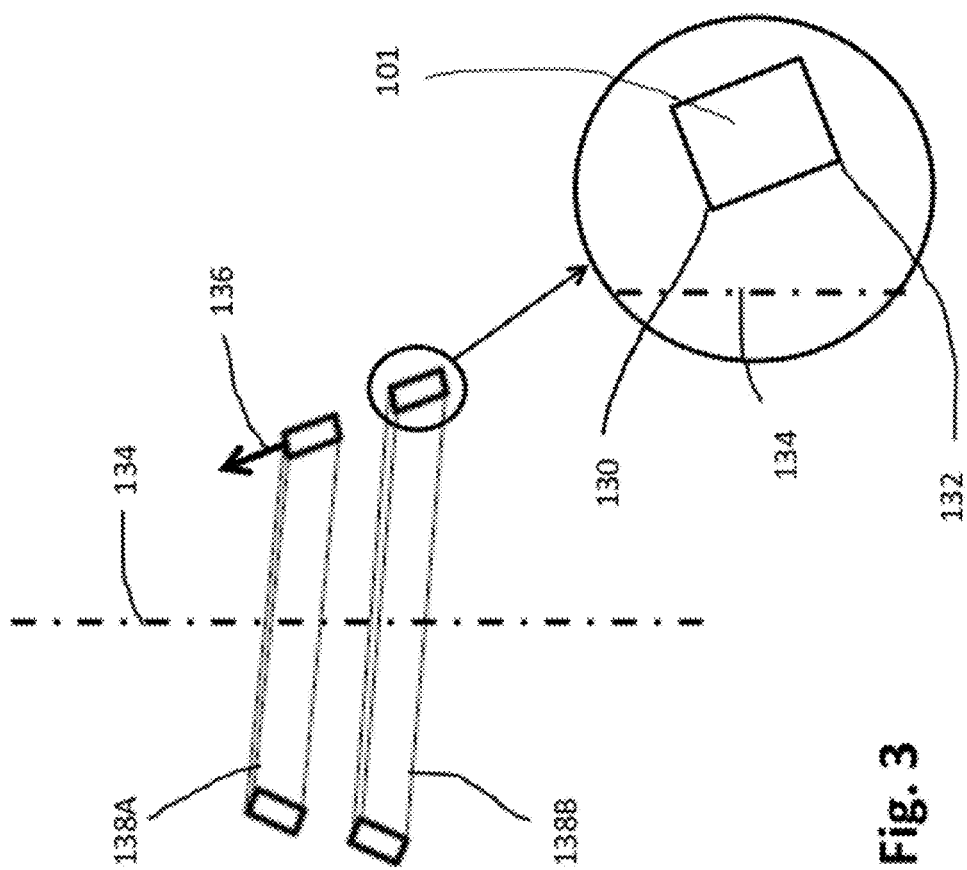
FIG. 3 is a cross-sectional and detail view of the probe tip assembly shown in FIGS. 1 and 2.

FIGS. 1 and 2 are schematic views intended to illustrate the basic operating principles of a probe tip 100 for use with in situ testing of the strength of a material 102. The probe tip 100 is essentially a coil spring that functions as a thread so as to be able to screw into the material 102, and thus is referred to herein as a "coil spring thread" 101.

In order to be able to quantify measurements, the coil spring thread 101 isolates a portion of the material 102 into a known geometric cross section. This is accomplished by the hollow nature of the coil spring thread 101, which, as it scores into the material, will surround a portion thereof. In the illustrated embodiment the coil spring thread 101 is helical so as to surround a cylindrical column 104 of the material 102, and thus the known geometric cross section in the illustrated embodiment will have a diameter and depth.

In order to determine the tensile strength of the material, the probe tip 100 must also function to apply a tensile stress to the isolated volume of the material such as cylindrical column 104. This accomplished by the cross-sectional profile of the coil spring thread 101, as will be discussed in greater detail below. It will be seen that when the coil spring thread 101 is rotated, the coil spring thread 101 will tend to pull itself into the material in a first longitudinal direction 106. In reaction, the material will tend to pull itself in an opposite longitudinal direction 108. (In other words, the coil spring thread 101 generates a longitudinal force to urge the volume of material longitudinally away from remaining material, this longitudinal force being resisted by adherence of the volume of material to the remaining material.) In order to measure the tension, the coil spring thread 101 is rigidly connected to a longitudinal member 110 which, while also rotating, is held in place relative to a fixed or moving reference position (the longitudinal member 110 may rotate in situ or descent relatively slowly as discussed in greater detail below). Thus, as the coil spring thread 101 pulls into the material the longitudinal member 110 will experience a stretching stress that can be measured by a strain gauge 112.

A method of measuring the subsurface tensile strength of the material is illustrated with respect to FIGS. 1 and 2. In FIG. 1, the probe tip 100 is disposed at a first position 114 within the material. A bore 116 may be drilled into the material 102 in order to bring the probe tip 100 to the first depth 114, or, the testing of the material may begin at its surface and the bore created in the process of testing the material. The coil spring thread is lowered and twisting somewhat into the material in order to be able bite into or grip the material. The longitudinal member 110 is then rotated, causing the coil spring thread 101 to pull into the material and thereby generate a stress on the longitudinal member 110 and a reactionary pull 108 in the material. The strain on the longitudinal member 110 is measured by the strain gauge 112, and will provide useful data as discussed below. As a result of the pulling force into the material, the coil spring thread 101 will move deeper into the material to a second depth 118 where the material fractures transverse (e.g., at region 120) to the longitudinal direction, as shown in FIG. 2. At this point, the strain on the longitudinal member 110 correlates to the maximum tensile strength of the material at the indicated depth. The process can be repeated again and again to measure the tensile strength of the material at successively deeper penetrations into the material, wherein the longitudinal member and probe tip are lowered together as a unit. Alternatively, instead of discretely moving the longitudinal member and probe tip to successively deeper positions in the material, it will be appreciated that the longitudinal member and probe tip may be continuously translated downwardly in order to generate a continuous tensile strength v. depth profile. In any case, any loose material caused by fracture is preferably withdrawn from the bore 116 or at least moved out of the way so as not to interfere with the next batch of material being tested as an isolated column. As discussed below, an auger with a hollow shaft may be used for this purpose.

The cross-sectional profile of the coil spring thread 101 is shown in greater detail in FIG. 3. The thread is preferably rectangular in cross-section, but oriented in such a way that the turns of the coil are angled to hold tightly to the material inside the coil, i.e., to the isolated portion of material scored by the coil such as cylindrical column 104, and slide past the material outside of the coil. More particularly, the generally rectangular cross-sectional profile of the thread includes a top corner 130 proximate the longitudinal member 106 and a diametrically opposed bottom corner 132 distal the longitudinal member 106. The thread is canted so that the top corner 130 is closer to a central axis 134 of the coil spring thread 101 than the bottom corner 132. The cant thus directs a reactionary force (represented by reference arrow 136) generated by the thread somewhat inwardly towards the portion of the material surrounded by the coil spring thread.

The coil spring thread 101 preferably includes at least two volutes 138. One volute 138A is proximate to the longitudinal member 110 and one volute 138B is distal to the longitudinal member 110. The distal volute 138B preferably has a diameter slightly larger than the proximate volute 138A so as to configure the coil spring thread slightly conical. The slight conical configuration is intended to provide grip to the material inside the coil, i.e., to the isolated portion of material scored by the coil such as cylindrical column 104, by scoring the material at a slightly inwardly offset peripheral position.

Figure 4:
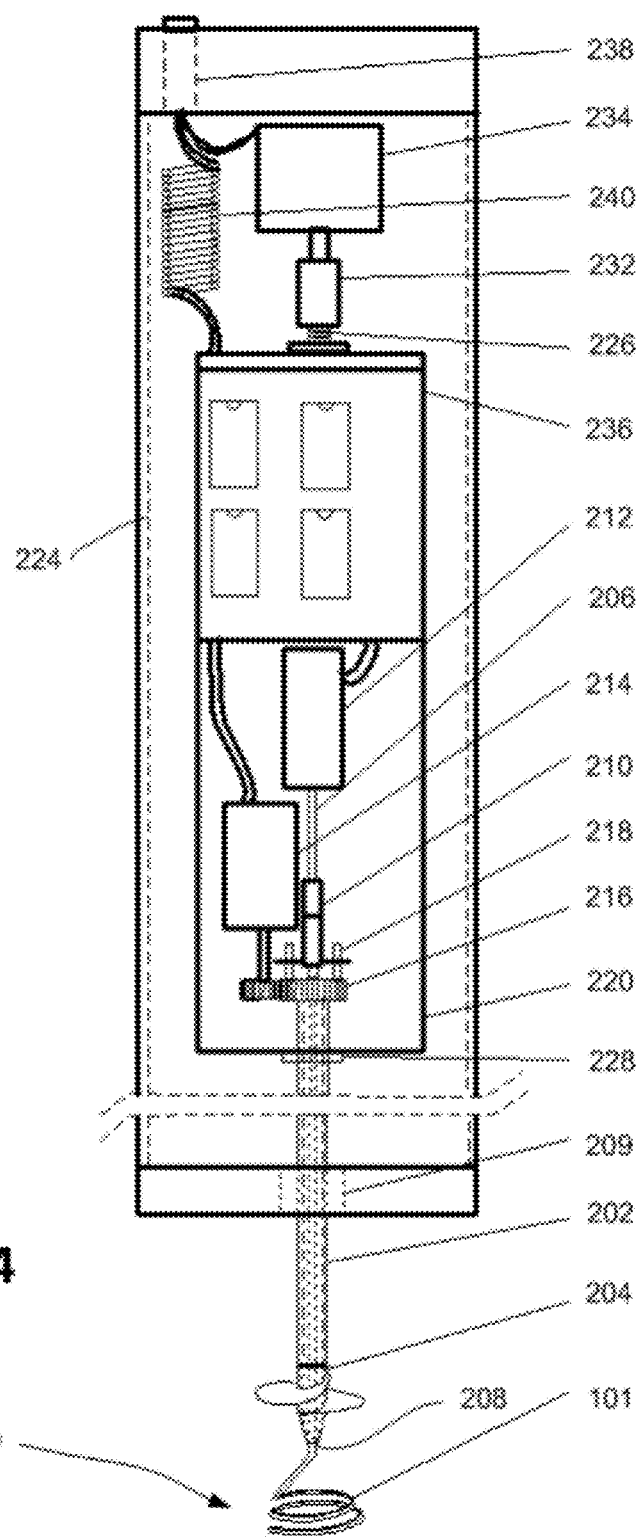
FIG. 4 is a front view of an apparatus (with cover removed) for rotating and translating the probe tip.
Figure 5:
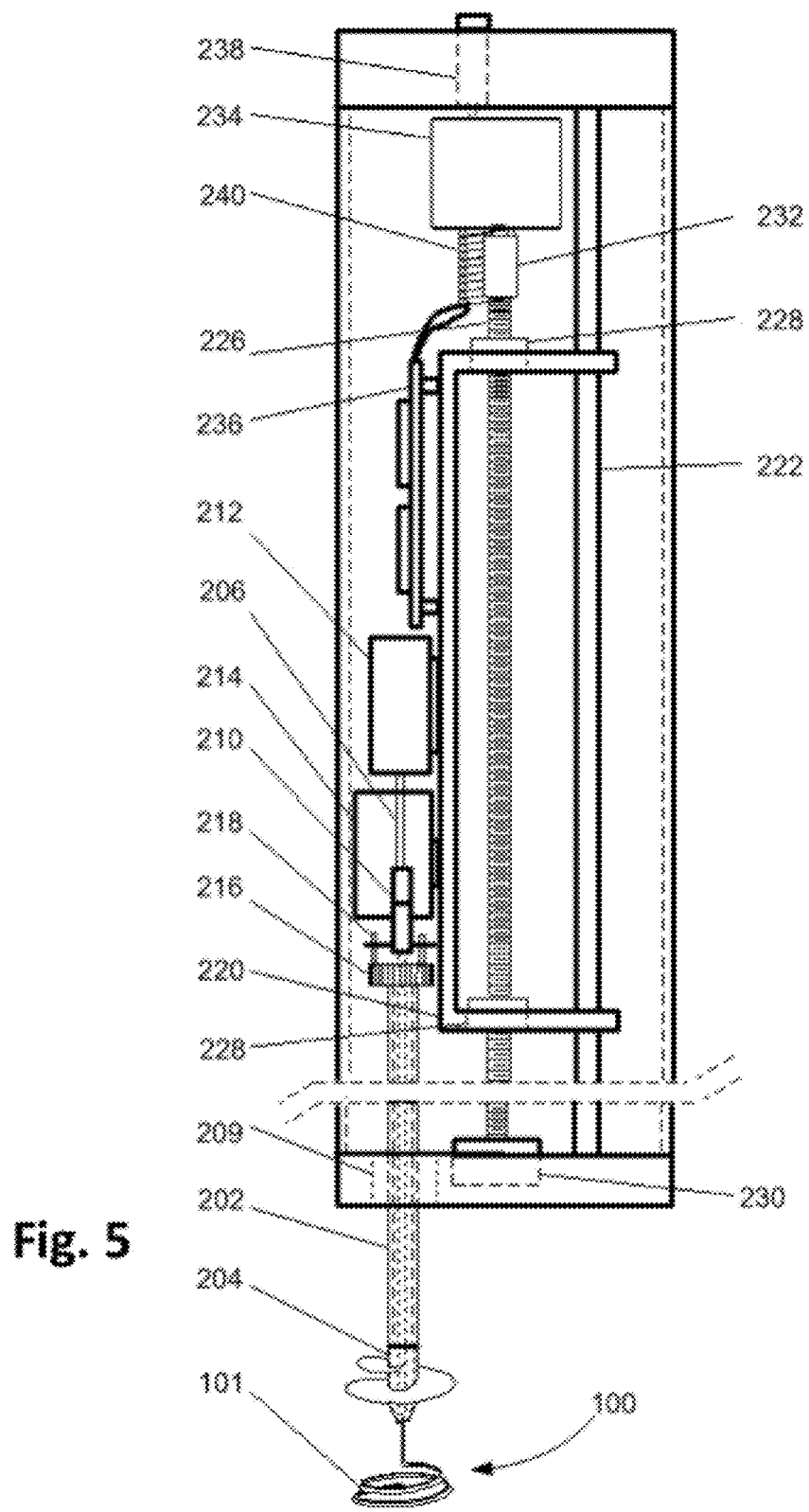
FIG. 5 is a side view of the apparatus shown in FIG. 4.

FIGS. 4 and 5 show an apparatus 200 which is designed to continuously move the probe tip 100 deeper into the material at a predetermined rate. The rate of translation is preferably less than a rate at which new material is drawn into the coil spring thread 101 as a consequence of the screw-like pull of the coil spring thread 101 into the material. In this manner, the apparatus 200 builds stress on an isolated column of the material as the probe is advanced into the material. The isolated column of the material breaks or fractures at its base, and as the probe tip is continuously translated deeper into the material the build-up of stress re-occurs to a successive isolated column of the material thereby enabling a continuous plot of the tensile strength of the material relative to the depth of the material. An auger-like device disposed above the probe tip 100 has a greater pitch than the coil spring thread 101 and thus removes any loose material by moving it away from the probe tip.

The apparatus 200 includes a hollow probe shaft 202 that is mounted for rotation in a frame 224 and extends through a seal 209 in the frame. An auger blade 204 is affixed to the outer wall of the hollow shaft 202. A longitudinal force transmission member 206, preferably made of carbon fibre, is disposed for rotation in the hollow shaft 202. The longitudinal member 206 slides with low friction through a seal 208 at the tip of the hollow shaft 202 and is rigidly affixed to probe tip 100. Thus, the probe tip 100 can be considered as a continuation of the longitudinal member 206.

At its upper end the longitudinal force transmission member 206 extends past the hollow probe shaft 202 and is connected to a swivel 210. Above the swivel, the longitudinal force transmission member 206 is attached to strain gage 212. A stepper motor 214 drives a gear train including output gear 216 that is attached to hollow probe shaft 202. Rotation of the stepper motor 214 causes hollow probe shaft 202 to rotate which causes the lower end of the swivel 210 to rotate by means of a low friction coupling 218. Rotation of lower end of the swivel 210 in turn causes the rotation of the longitudinal force transmission member 206 and attached probe tip 100. (Those skilled in the art will understand that in the alternative a separate motor and gear assembly may be used to rotate the longitudinal force transmission member 206 independent of the hollow probe shaft 202.) While low friction coupling 218 rotates, its longitudinal motion is not impeded so that force at probe tip 100 is transmitted with little friction to the strain gauge 212.

The translational movement of the probe tip 100 is provided by a moving stage 220. The strain gauge 212 and stepper motor 214 are mounted to the moving stage 220, thus suspending the hollow probe shaft 202 and longitudinal force transmission member 206 therefrom. The moving stage 220 is slidably mounted through low friction bushings to a stage guide such as pole 222 installed in the frame 224. The moving stage 220 is linearly translated by means of a threaded rod 226 which turns in threaded inserts 228 affixed to the moving stage 220. The threaded rod 226 rotates in situ atop bearing 230 disposed at the bottom of the frame. At the top of the threaded rod 226, a coupling 232 connects the threaded rod 226 with a second stepper motor 234 that is affixed to the frame 224. Consequently, rotation of the threaded rod 226 in situ results in the linear translation of the moving stage 220.

An electronic control unit (ECU) 236 is mounted to the moving stage 220. A power/data connection cable 238 provides power to electronic 6 through expandable wire coil 3. The ECU 236 drives and synchronizes the stepper motors 214, 234, stores data output by the strain gage 212 and position of probe tip 100, and transmits these data through the power/data connection cable 238.

Figure 6:
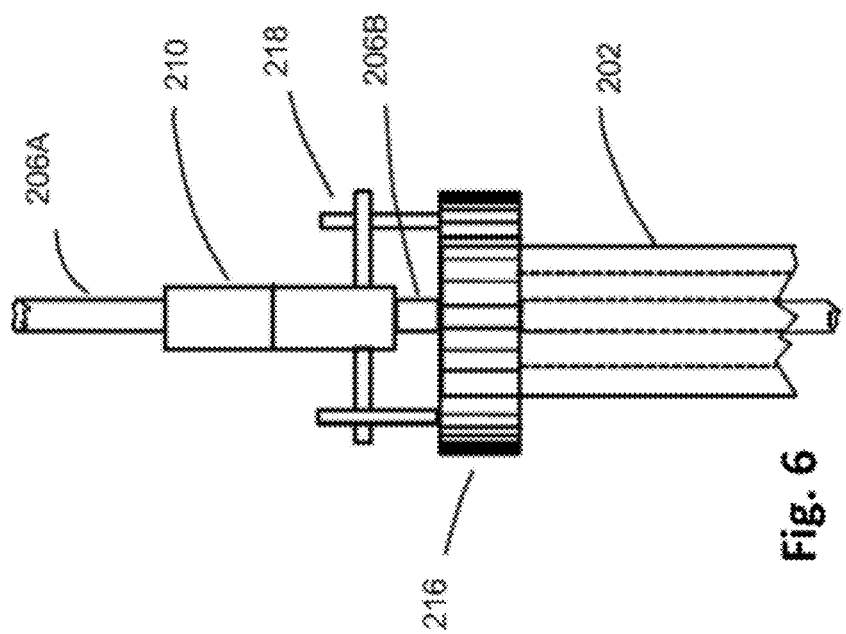
FIG. 6 is a detail view of a low friction coupling employed in the apparatus shown in FIG. 4.

FIG. 6 is a detail view of the low friction coupling 218 wherein the lower part of swivel 10, force transmission member 206b and probe tip 100 is rotated and at the same time, the axial force at probe tip 100 is transmitted to strain gage 212 with low friction.

In this embodiment the ECU preferably moves the probe tip 100 downwardly into the test material at a rate that is slower than the rate new sample material is drawn into the coil spring thread 101 due to its screw-like advance into the material. The result is that stress builds up in the probe tip and is opposed by stress build up in the isolated column of in the center of the probe tip. This stress is measured by the strain gauge that is connected to the probe tip by the carbon fiber longitudinal force transmission member. Typically the column of material in the center of the probe tip will break at its base and the maximum stress at the point of breaking, which corresponds to a measure of the strength of the material, is recorded by the ECU.

Figure 7:
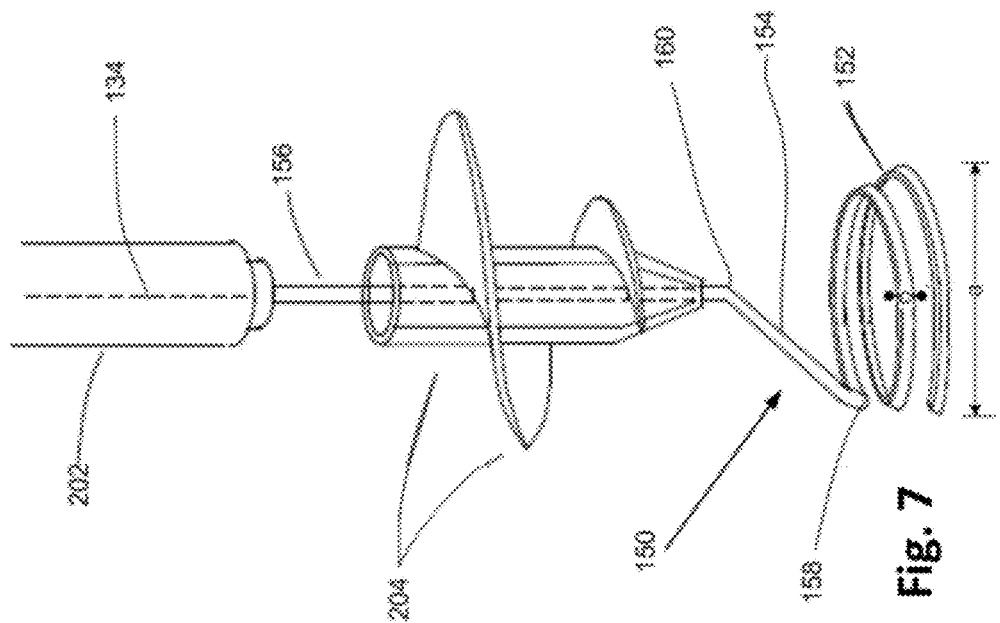
FIG. 7 is a detailed perspective view of a probe tip assembly used to measure tensile strength in marine sediment beds.

Referring additionally to FIG. 7, the probe tip 150 was constructed of a 0.0008 m diameter stainless steel wire 152 fabricated in the shape of a slightly conical spring (10° to the longitudinal axis 134) with its largest diameter portion a, being 0.01 m OD, facing downward, as indicated in FIG. 6. The wire 152 composing the spring was flattened to create a thread with a cross-sectional length to width ratio of 3:1. Coil spacing c (center on center) was 0.0028 m. The longer side of the rectangular cross section of the thread is canted upward to the inside (toward the longitudinal axis 134) at 45°. The canting of the flat portion of the coil spring thread caused the inside of the coil spring thread to bite into and hold an isolated cylinder of the sediment against vertical slip, while allowing the outside of the coil spring thread to slip past the sediment to the outside of the coil spring thread. Thus when force is applied to the probe tip 150, the coil spring thread held tightly to the sediment inside the coil whilst allowing the coil to slip past the sediment on the outside. Above the coil spring thread the wire 152 provides a transition portion 154 for connecting the coil spring thread to a longitudinal member 156. In the transition portion 154, the wire 152 is cylindrical in cross-section and is bent at 45° (ref. No. 158) toward the inside/center of the coil spring thread. At the central longitudinal axis 156, the wire is again bent 45° (ref. No. 160) so as to be concentric with the coil spring thread and connect inline to the longitudinal member 156 which is also disposed along the central longitudinal axis.

The tensile strength of marine sediment beds was investigated using the apparatus 200 described above and the probe tip 150. The rate of advance of the probe tip into sediment is programmable, but was typically set to about 0.01 m/min. As the probe tip advanced, it defined the circumference of a cylindrical column of sediment approximately 0.01 m in diameter. Fracture occurred at about 0.002 m intervals at the base of the cylindrical column, where the cylindrical column is scored to a depth a of approximately 0.0008 m. About 1.5 to 2.0 coils typically engaged the cylindrical sediment column when it separated at its base. To ensure that sediment separated by the probe did not contribute to the fracture signal, loose sediment was removed from the hole by the auger 204 at a rate faster than the linear advance of the probe tip.

The fracture probe was calibrated by attaching a lightweight container to the probe tip, to which known weights of water were added. The calibration process correlates strain to applied force.

In operation, stress is determined from the diameter d of the cylindrical sediment column, depth of scoring a, and the calibrated strain-gauge output. Interpretation of results in terms of $K_{IC}$ then comes directly from the following equations (Oster and Mills 2000):

$$K_{IC} = \sigma_C Y (\pi a)^{1/2}$$

where $Y = 3.0149 + 2.4902\ e^{-166.26(B)} - 51.624B + 722.92 B^2 - 5342.9 B^3 + 21757 B^4 - 45123.3 B^5 + 37900.2 B^6$ and where $B = a/d$, a is crack depth or depth of scoring, d is cylinder diameter and $\sigma_c$ is the critical stress at fracture.

The results from the in situ probe compared favourably to $K_{IC}$ values obtained from the laboratory-based bubble method (Johnson et al. 2002) and the modified engineering method.

Those skilled in the art will appreciate that the detailed configuration of the probe tip will vary depending on the nature of the material to be tested. The principal considerations here are that the probe tip needs to be sized such that it is large enough to render edge effects small, and yet small enough that the grip on the surrounded column of material is sufficient to cause failure at the base of the column. If the probe tip is too great in diameter, it will slip and merely scrape the outer part of the column rather than causing it to fail at the base. For a cylindrical column, the effects at the side of the cylinder change as the first power of the diameter, while the cylinder strength at the base changes as a higher power of the diameter.

Those skilled in the art will also understand that the above equation for $K_{IC}$ will also vary depending on the geometry of the probe tip. For other geometries, e.g., a notched rectangle subjected to three point bending, or a notched cylinder, Y would be a different function, but the remainder of the $K_{IC}$ equation would remain the same. The $K_{IC}$ equation applies to elastic materials which, as a class, tend to fail by fracture. Many sediments, soils, snow, mud and fruits and vegetables fail in this way. Other materials may behave plastically, in which case the $K_{IC}$ would not apply, but other useful data may be extracted in this case.

The foregoing embodiments employed an approach where, from a relative point of view, the longitudinal member and coil spring thread are fixed in relation to a longitudinal position and the coil spring thread is pulled into the material. In alternative embodiments the coil spring thread may be driven into the material where the longitudinal member is free to move longitudinally, or is driven into the material at the same or somewhat greater rate than the coil spring thread is pulled onto the material. Then, a force may be applied to the longitudinal member and coil spring thread to urge the volume of material held by the coil longitudinally away from the remaining material. This longitudinal force may be increased until the volume of material held by the coil separates from the remaining material, and the strain on the longitudinal member at that point can be measured. The apparatus 200 may be utilized in this mode, where the probe tip 100 is first drilled into the material and then the moving stage is controlled to pull the longitudinal member and coil spring thread upwards until the volume of material held by the coil spring thread factures, at which point the strain in the longitudinal member is measured and correlated to the fracture strength of the material. In addition, other useful information may be extracted prior to fracture, e.g., there should also be a linear portion of stress vs strain and the slope of that curve would indicate Young's modulus. The process may be repeated at successively deeper positions in the material.

In the embodiments described above, the coil spring thread constituted the portion of the apparatus that was driven into and engaged the column of material. It will be noted that other types of material engagement head are possible. For example a material engagement head may be provided that is a hollow rectangular shape or a hollow cylindrical shape, with elements that are shaped to engage the volume of material contained therein. Such elements might resemble the grating elements on a cheese grater, but while a cheese grater has the grating elements oriented to engage material sliding down the outside surface of the cheese grater, these elements would be oriented towards the inner volume of the material engagement head so as to engage the volume of material contained therein. In such an embodiment, the material engagement head would be movable by a motor system to drive it into the material so as to hold and engage a volume of material. The material engagement head could be driven by direct longitudinal force into the material or by rotation or by a combination of the two or by any suitable type of force. The motor system would be operable to exert a longitudinal force on the material engagement head to urge the volume of material away from remaining material. The longitudinal member which has the material engagement head thereon may be engaged with a strain gauge or any other suitable sensor for use in determining the longitudinal force with which the material engagement head urges the volume of material away from the remaining material. The motor system would progressively increase the longitudinal force until the volume of material separates from the remaining material. The controller can be configured to receive signals from the strain gauge (or whatever sensor is provided) and is programmed to determine the force used to separate the volume of material from the remaining material so as to determine the tensile strength of the material. In this embodiment, if the material engagement head is not needed to be rotated then a special coupling that permits rotation and longitudinal movement is not needed in the longitudinal member. The motor system could employ one motor or more than one motor, as needed based on the specific type of material engagement head used and whether it requires both longitudinal movement and rotation, and based on other factors.

In the embodiment shown in the figures, the motor system includes the two motors 214 and 234.

Likewise, those skilled in the will appreciate that a variety of modifications may be made to the preferred embodiments discussed herein without departing from the spirit of the invention.

We claim:

1. A probe for determining the tensile strength of a material, comprising:
   a housing;
   a longitudinal member rotatably journaled in the housing, the longitudinal member defining a longitudinal axis;
   a coil spring thread, rigidly connected to the longitudinal member, and disposed external of the housing;
   a motor for rotating the longitudinal member and coil spring thread, wherein, upon rotation of the longitudinal member and the coil spring thread, the coil spring thread is pulled into the material generating a reactionary pull in the material and causing a stress on the longitudinal member;
   a strain gauge for measuring the strain on the longitudinal member; and
   a controller connected to the strain gauge for determining the tensile strength of the material based on the strain experienced by the longitudinal member.

2. A probe according to claim 1, wherein the controller measures the strain experienced by the longitudinal member when the material fractures due to the reactionary pull of the material.

3. A probe according to claim 1, wherein the coil spring thread is configured such that the reactionary force generated thereby is directed inwardly towards a column of material surrounded by the coil spring thread.

4. A probe according to claim 1, wherein the coil spring thread has a generally rectangular cross-sectional profile including a top corner proximate the longitudinal member and a diametrically opposed bottom corner distal the longitudinal member, the coil spring thread being canted so that the top corner is closer to the longitudinal axis than the bottom corner.

5. A probe according to claim 4, wherein the coil spring thread is helical and concentric with the longitudinal member, and a transition portion continues the longitudinal member and connects it with a first volute of the coil spring thread.

6. A probe according to claim 5, wherein the helical coil spring thread has at least two volutes, one volute being proximate to the longitudinal member and one volute being distal to the longitudinal member, the distal volute having a diameter larger than the proximate volute.

7. A probe according to claim 4, including a hollow shaft rotatably mounted to the housing, the longitudinal member being disposed within the hollow shaft and the coil spring thread being disposed external of the hollow shaft, the hollow shaft having an auger blade connected to the outer wall of the shaft, the hollow shaft being rotated by the motor or an another motor.

8. A probe according to claim 7, including a moving stage mounted within the housing to translate linearly and a motor for driving the moving stage, wherein the hollow shaft and the longitudinal member depend from the moving stage, and the controller controls the rate of decent of the moving stage.

9. A probe according to claim 8, wherein the controller controls decent of the hollow shaft such that the rate of decent is less than the rate at which new material is fed into the coil spring head, thereby enabling stress to build up in the column of material surrounded by the coil spring thread until the column fractures.

10. A method for determining the tensile strength of a material, comprising:
(a) provisioning a probe comprising a housing and a longitudinal member rotatable in the housing, the longitudinal member terminating in a coil spring thread disposed external to the housing, the coil spring thread defining a column;
(b) positioning the coil spring thread at a first depth in the material;
(c) rotating the longitudinal member so as to pull the coil spring thread into the material and generate a reactionary pull substantially in a corresponding columnar portion of the material scored by the coil spring thread, the terminating end of the coil spring thread being pulled to a second depth;
(d) measuring a strain on the longitudinal member as the coils spring head moves to the second depth; and
(e) determining the strength of the material based on the measured strain.

11. A method according to claim 10, wherein at the second depth the columnar portion of the material fractures, and the fracture strength of the material is determined based on the measured strain at the second depth, a difference between the first and second depths, and a diameter of the coil spring thread.

12. A method according to claim 11, wherein the coil spring thread is configured such that the reactionary force generated thereby is directed inwardly towards the columnar portion of the material surrounded by the coil spring thread.

13. A method according to claim 12, wherein the coil spring thread has a generally rectangular cross-sectional profile including a top corner proximate the longitudinal member and a diametrically opposed bottom corner distal the longitudinal member, the coil spring thread being canted so that the top corner is closer to a central axis of the coil spring thread than the bottom corner.

14. A method according to claim 13, including continuously moving the longitudinal member and coil spring thread deeper into the material at a predetermined rate, the predetermined rate being less than a rate at which new material is drawn into the coil spring thread as a consequence of continuously rotating the longitudinal member, thereby building stress on a successive columnar sample of the material as the probe is advanced into the material, and repeating steps (d) and (e) to thereby plot the tensile strength of the material relative to the depth of the material.

15. A method according to claim 14, wherein the probe creates a bore, and including clearing the bore out of any loose material created by the fracturing thereof.

16. A method according to claim 10, including successively increasing the first depth and repeating steps (c) to (e) so as to thereby plot the tensile strength of the material relative to the depth of the material.

17. A method according to claim 16, wherein the coil spring thread is configured such that the reactionary force generated thereby is directed inwardly towards the columnar portion of the material surrounded by the coil spring thread.

18. A method according to claim 17, wherein the coil spring thread has a generally rectangular cross-sectional profile including a top corner proximate the longitudinal member and a diametrically opposed bottom corner distal the longitudinal member, the coil spring thread being canted so that the top corner is closer to a central longitudinal axis of the coil spring thread than the bottom corner.

19. A method according to claim 18, wherein the coil spring thread is helical and concentric with the longitudinal member, wherein a transition portion continues the longitudinal member and connects it with a first volute of the coil spring thread.

20. A method according to claim 19, wherein the helical coil spring thread has at least two volutes, one volute being proximate to the longitudinal member and one volute being distal to the longitudinal member, the distal volute having a diameter larger than the proximate volute.

* * * * *